(12) United States Patent
Schwamb

(10) Patent No.: US 11,679,485 B2
(45) Date of Patent: Jun. 20, 2023

(54) POWERED INSTRUMENT

(71) Applicant: Medtronic Xomed, Inc., Jacksonville, FL (US)

(72) Inventor: Jeffrey M. Schwamb, Saint Marys, GA (US)

(73) Assignee: Medtronic Xomed, Inc., Jacksonville, FL (US)

(*) Notice: Subject to any disclaimer, the term of this patent is extended or adjusted under 35 U.S.C. 154(b) by 49 days.

(21) Appl. No.: 16/749,081

(22) Filed: Jan. 22, 2020

(65) Prior Publication Data

US 2021/0220983 A1 Jul. 22, 2021

(51) Int. Cl.
    *B25F 5/00*     (2006.01)
    *A61B 17/00*     (2006.01)
    *B25F 3/00*     (2006.01)

(52) U.S. Cl.
    CPC .............. *B25F 5/001* (2013.01); *A61B 17/00* (2013.01); *B25F 3/00* (2013.01); *A61B 2017/00464* (2013.01)

(58) Field of Classification Search
CPC . B25F 5/001; B25F 3/00; A61B 17/00; A61B 2017/00464
See application file for complete search history.

(56) References Cited

U.S. PATENT DOCUMENTS

| | | | |
|---|---|---|---|
| 5,993,454 A | 11/1999 | Longo | |
| 2017/0219087 A1* | 8/2017 | Herr | F16H 57/08 |
| 2019/0125384 A1* | 5/2019 | Scheib | A61B 17/29 |
| 2020/0305893 A1 | 10/2020 | Nino | |
| 2021/0172499 A1* | 6/2021 | Nino | F16H 55/06 |

FOREIGN PATENT DOCUMENTS

| | | |
|---|---|---|
| WO | 2019035088 A1 | 2/2019 |
| WO | 2019090151 A1 | 5/2019 |

OTHER PUBLICATIONS

International Search Report and Written Opinion regarding International Application No. PCT/US2021/013900, dated Apr. 30, 2021.
International Preliminary Report on Patentability regarding PCT/US2021/013900, dated Aug. 4, 2022.

* cited by examiner

*Primary Examiner* — Daniel Jeremy Leeds
(74) *Attorney, Agent, or Firm* — Carter, DeLuca & Farrell LLP

(57) ABSTRACT

Disclosed is an instrument assembly for performing a procedure. The instrument assembly may include a powered motor for moving, such as rotating, a tool tip. The instrument assembly may include a transmission or a gear assembly to provide varying speed and/or torque to the tool tip.

8 Claims, 10 Drawing Sheets

POWERED INSTRUMENT

FIELD

The subject application relates to an instrument assembly and system, and particularly to a powered instrument having a plurality of final gear ratios.

BACKGROUND

This section provides background information related to the present disclosure which is not necessarily prior art.

A tool or tool tip may be operated in a selected manner to perform a procedure on a subject. The tool may include a selected bit or tip, such as a grinding burr, drilling bit, or other appropriate tip. The tip may be powered in a selected manner, such as through rotation from a motor. The motor may be an appropriate motor, such as an electric motor, hydraulic motor, or other appropriate motors to provide rotational force or torque to the instrument. The tool tip may then be rotated based upon the power provided by the motor to perform a procedure.

SUMMARY

This section provides a general summary of the disclosure, and is not a comprehensive disclosure of its full scope or all of its features.

An instrument assembly may be used to power a tool or tool tip. The tool tip may include any appropriate tool tip such as a cutting burr, a grinding burr, a boring tip, etc. The tips are generally powered at a selected speed by operating a motor to drive a transmission or drive shaft to rotate the tool. Disclosed is an instrument assembly that includes a powered handle portion that may operate a plurality of tools at a plurality of selected speeds, torque force values, and combinations thereof.

The power handle assembly generally includes a motor that may be powered in a selected manner such as an electrical motor, a pneumatic motor, a hydraulic motor, or the like. The motor may be operated or controlled by a user and is generally configured to be held by a hand of a user. The user may operate the motor to power or rotate a tool at a selected speed and/or torque for performing a procedure on a subject.

The instrument assembly generally includes a drive shaft extending from the motor that may engage a tool directly and/or power a selected gearing mechanism to power a second shaft. The differing shafts may allow the single motor to be operated at a selected single setting, but apply different speeds and/or torques to a selected tool. Thus, a single motor may be used to power a plurality of tools at different speeds and/or torque forces to achieve selected results with different tools.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
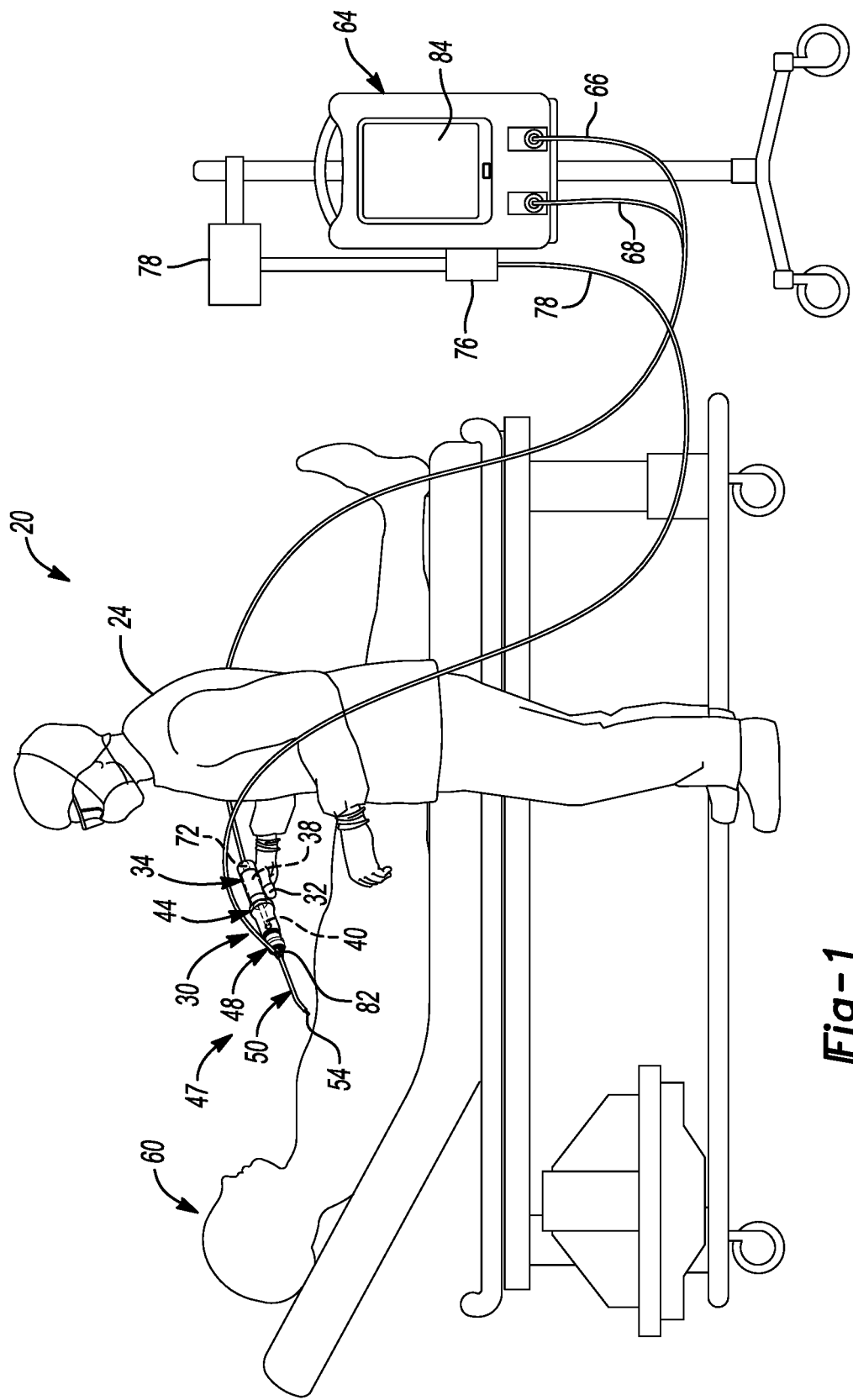
FIG. 1 is a schematic environmental view of an instrument assembly in a procedure setting.
Figure 2:
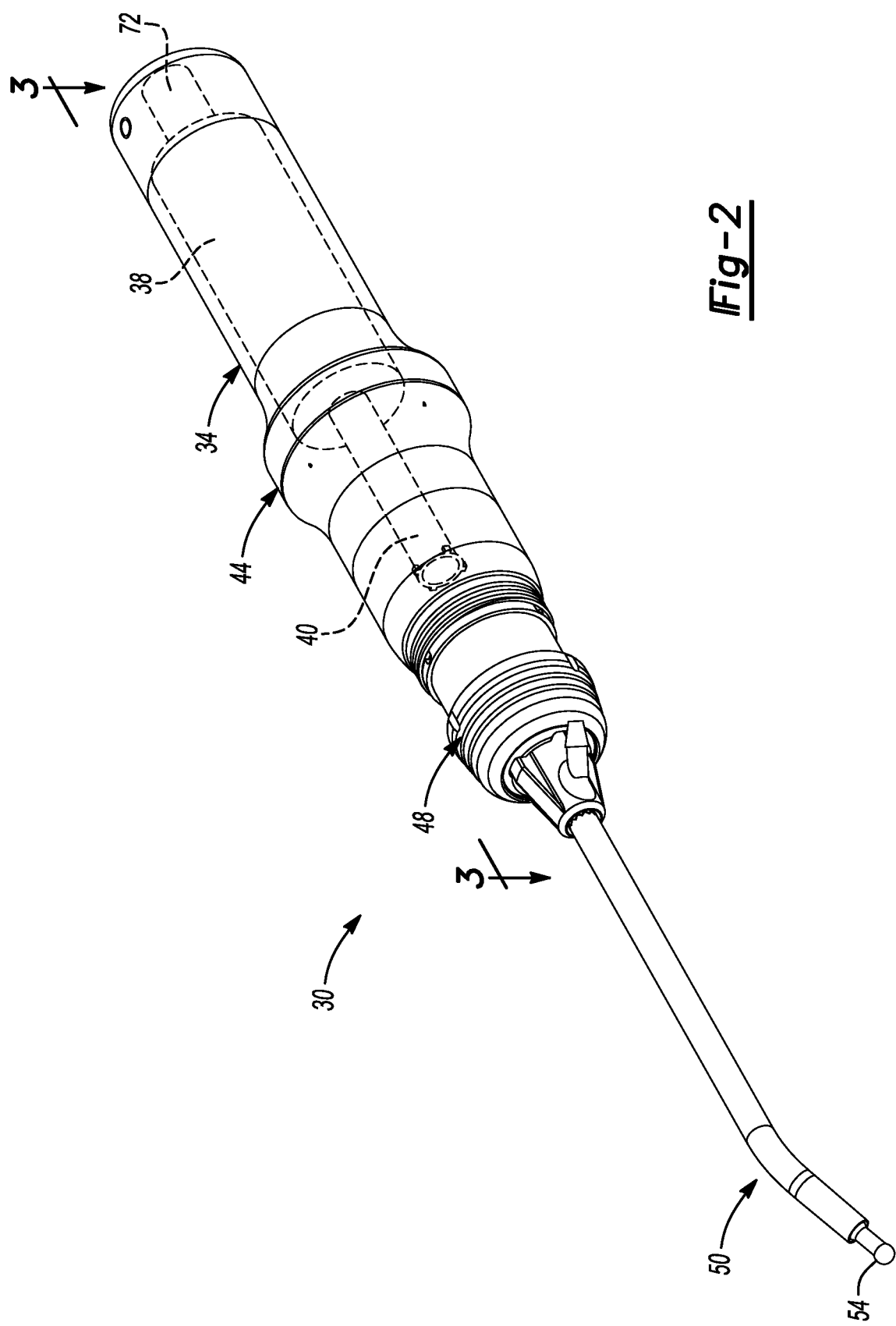
FIG. 2 is a perspective view of an instrument assembly.

With initial reference to FIG. 1 and FIG. 2, an instrument assembly system 20 is illustrated. The system 20 may be operated by a user 24, as discussed further herein. In various embodiments, the system 20 includes a hand held or powered instrument assembly 30 that may be held by a hand 32 of the user 24. Generally, for example, the user 24 may grasp a housing portion or handle portion 34 that may be used to house a motor 38. Extending from the motor 38 may be a drive shaft 40. Connected to the handle portion 34 may be a selected number of components, such as a gear transmission section or portion 44, a collet or tool connection section or portion 48, and a tool or working end portion 50. The tool portion 50 may include a working tip or end 54. The distal end or tip 54 may be used to perform a procedure on a subject 60. The subject 60 may be any appropriate subject, such as an inanimate or mechanical subject, a living subject, or the like. In various embodiments, as illustrated in FIG. 1, the subject 60 may be a human subject.

The system 20 may further include a control assembly or portion 64 that may be similar to the Integrated Power Console (IPC®) instrument control system or power console sold by Medtronic, Inc. having a place of business in Minneapolis, Minn. The console or control 64 may include various connections for connection to the instrument assembly for various purposes. In various embodiments, for example, a power connection 66 may be provided to power the motor 38. The motor 38 may be powered in any appropriate manner such as an electronic power, pneumatic power, or the like. Thus, the motor 38 may be powered to operate or rotate the distal tip 54 of the tool 50, in an appropriate manner. Various other connections may include a suction connection 68. The suction connection 68 may connect to a central bore or cannula 72 that extends through the motor 38 and the shaft 40. The suction may be drawn through a selected portion of the instrument assembly 30, as is generally known in the art. Instruments with various drill and instrument assemblies include the Visao® Otologic Drill, the Midas Rex® stylus drills, certain instruments may further include suction such as the Straightshot® M4

Microdebrider, also by Medtronic, Inc. having a place of business in Minneapolis, Minn.

The user 24 may operate the instrument assembly 30 in any appropriate manner, such as with remotes connected to the console 64, controls on the instrument assembly 30, or any other appropriate way. The console 64, however, may be used to provide power and selected features to the instrument assembly 30. Thus, the user 24 may power on and off the motor 38 directly via the console 64 and/or with controls separate from but in communication with the console 64 and associated with the instrument assembly 30.

In various embodiments, irrigation may also be provided to the instrument assembly 30. The console 64 may include a pump assembly 76 that is configured to pump a selected irrigation fluid from a source 78 through an irrigation line or tube 78 that is connected to an irrigation port 82 on the instrument. The console 64 may also be used to power and/or control the irrigation flow to the instrument assembly 30, also in a manner that is generally understood in the art, including any instrument assemblies as discussed above. The console 64 may, therefore, be used to power or control various features of the instrument assembly 30 and provide feedback to the user 24, such as with a display screen 84.

With continuing reference to FIGS. 1 and 2 and additional reference to FIGS. 3-5, the instrument assembly 30 will be described in greater detail. The instrument assembly 30 may be used for various procedures, such as various ear, nose and throat procedures on the subject 60. As is generally understood by one skilled in the art, procedures may include encountering and/or affecting different types of tissue in the subject 60. For example, during a selected nose or nasal procedure, the user 24 may select or desire to remove and/or affect soft tissue and/or hard tissue. Accordingly, the instrument assembly 30 may be operated in a plurality of modes and configurations, as discussed further herein, based upon a selection by the user 24.

Affecting soft tissue may be most efficiently or effectively performed with a high torque applied to the tool 50, including the tool tip 54. Procedures on hard tissue may be most effectively or efficiently performed with a high speed delivered through the tool tip 54. For example, effective speeds for hard tissue (e.g. bone) may be about 30,000 rotations per minute (rpm) to about 90,000 rpm, but not require a torque as great as 16 ounce-inches (oz-in). Effective torque for soft tissue (e.g. cartilage, adipose, etc.) may be about 16 oz-in to about 50 oz-in. Accordingly, operating the tool assembly 30 in a plurality of manners or modes may allow for effective operation on the subject 60 in an efficient manner by allowing for operation of the tool tip 54, or selected plurality of tool tips 54, in either one of the selected high speed or high torque configuration.

In various embodiments, high torque may include torque that is greater than or equal about 200 inch ounces (in-oz). It is further understood, however, that high torque may be any torque that is selected to be higher than a lower torque mode or configuration of the instrument assembly 30. In various embodiments, for example, a low torque configuration of the instrument assembly 30 may include torque that is about 20 inch ounces to about 40 inch ounces, including about 25 inch ounces. High torque may include, therefore, a torque that is about three times to about ten times, including about five times greater than the low torque configuration.

A high-low speed configuration of the instrument assembly 30, may also include any selected first and second, or a plurality of speed configurations. In various embodiments a high speed configuration may include a speed of about 20,000 to about 100,000 rotations per minute (RPM), including about 30,000 RPMs to about 90,000 RPMs, of the tool tip 54 and/or the drive shaft 40. At the high speed the torque may be lower than at lower speeds. A low speed, therefore, may be some fraction thereof, such as about 50% to about 2% of the high speed, including about 2,000 RPMs to about 15,000 RPMs of the tool tip 54, including about 2,500 RPMs to about 10,000 RPMs. Nevertheless, the tool tip 54 may be rotated at two or more speeds that may be any appropriate differential between the two and may be referred to as a high speed and a low speed.

The instrument assembly 30 may include the housing or handle 34, as discussed above, and may be grasped or held by the user 24. The gear housing assembly 44 may be connected, such as removably connected, to the handle 34. The gear housing assembly 44 may be removably attached to the handle of the motor housing such as via a threaded engagement between the gear housing 44 and the motor housing 34. For example, as shown in FIG. 3, the motor housing 34 may have a distal end 90 that includes an internal thread 92. The gear housing 44 may include a proximal end 96 that includes an external thread 98. Thus, the gear housing 44 may be removably attached to the handle assembly 34. The handle assembly 34 may include the motor 38 positioned therein in any appropriate manner. The motor 38 may be used to power or rotate the drive shaft 40, as discussed further herein.

The instrument assembly 30 may further include the tool end or portion 48. The tool end or portion 48 may be removably connected to the gear housing 44 in an appropriate manner, such as with a selected thread. The gear assembly housing 44 may include a distal end 100 that includes an internal thread 102 and the tool portion 48 may include a proximal end 106 that includes an external thread 110. Thus, the tool portion 48 may be removably connected to the gear housing 44, such as by threadibly engaging the threads 110 and 102.

The tool assembly 50 may be provided as a disposable or single use tool assembly. Thus, the tool assembly 50 may be selectively connected to the gear housing 44 via the connection portion 48 for a selected portion of a procedure on the subject 60 and then removed from the gear housing 44 for an alternative or different portion of the procedure, as discussed further herein. The tool assembly 50, therefore, may be used for a single use portion of the procedure on the subject 60 and the disposed or at least partially disposed (e.g. by dismantling the tool assembly 50). It is understood that the tool assembly 50 may be used for multiple portions of the procedure on the subject 60 and therefore may be removed and reattached to the gear housing 44, but is understood to be removably attachable to the gear housing 44.

Figure 2A:
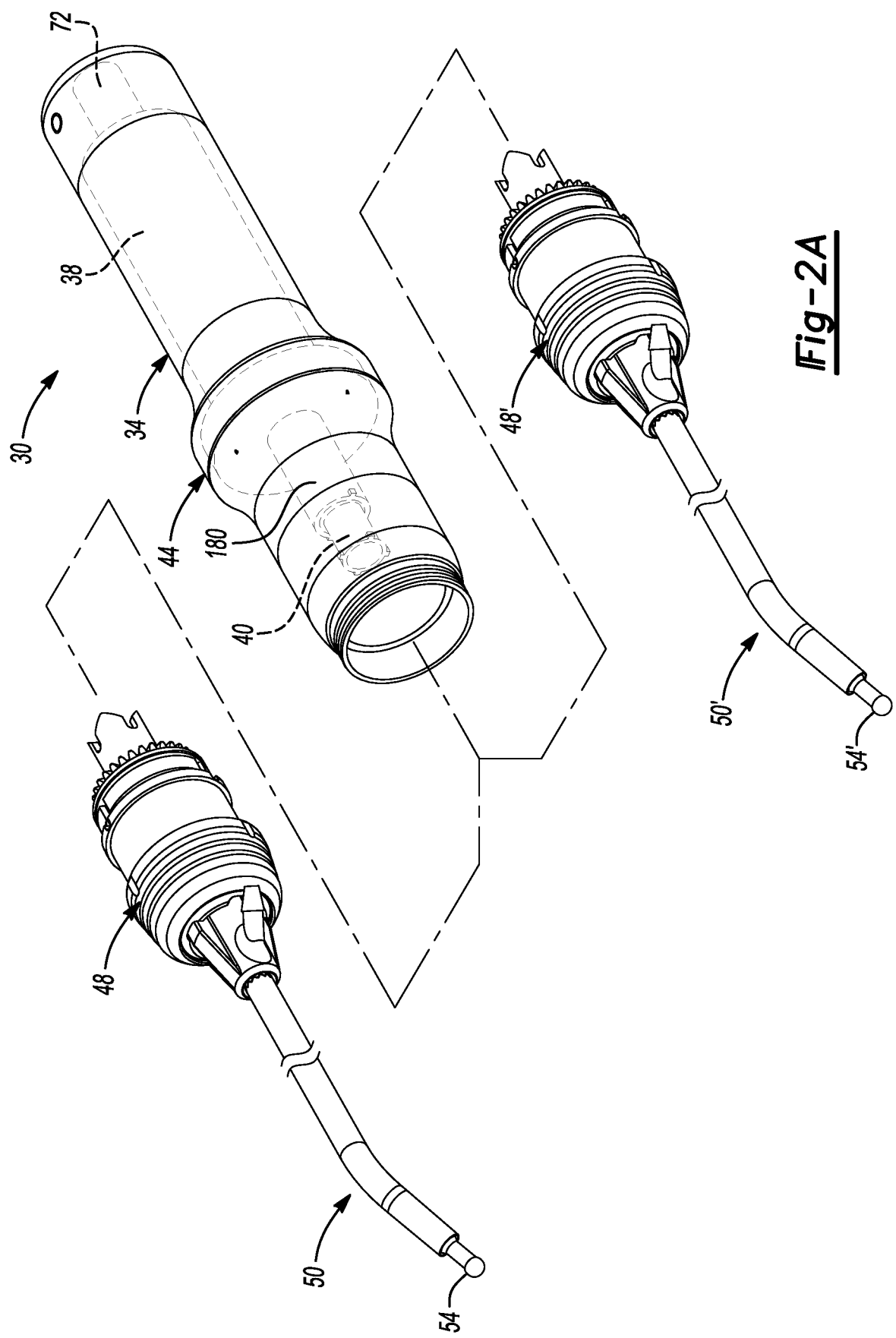
FIG. 2A is an exploded view of a kit of a first and second tool portions of the instrument assembly.

Turning brief reference to FIG. 2A, the instrument assembly 30 may include a kit or plurality of tool portions, such as a first tool portion 50 and a second tool portion 50'. Both of the tool portions 50, 50' may include respective connections portions 48, 48'. As discussed herein, each tool 50, 50' may separately and/or sequentially selectively engage the drive shaft 40 or a second drive shaft 180. The separate tools 50, 50' are different tools and may include different working tips 54, 54'. Each tip 54, 54' may operate most effectively and efficiently at a different torque and/or speed. Both of the tools 50, 50' may connect to the single handle 34 and motor 38.

As discussed herein, the instrument assembly includes two drive shafts 40, 180. Each drive shaft may separately and individually engage the separate tools 50, 50'. The different drive shafts 40, 180 may provide different torque and speed (e.g. rotations per minute (RPMs)) to the tools 50, 50' when engaged to the different drive shaft 40, 180. Herein is described the exemplary instrument assembly 30 including two or more drive shafts to provide different torque and/or speed from the motor 38. Further, both shafts 40, 180 may be co-axial and concentric to one another, as discussed herein.

Figure 3:
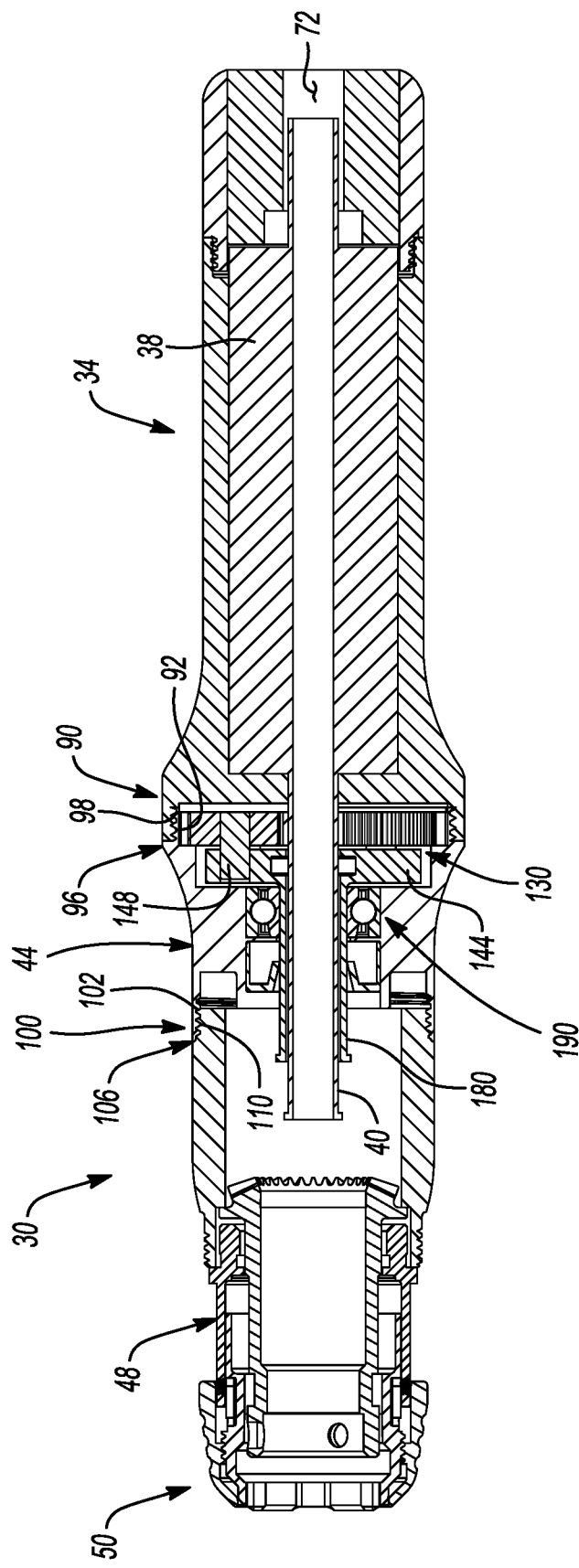
FIG. 3 is a cross-sectional view of the instrument assembly taken along line 3-3 of FIG. 2.

With further reference to FIG. 3, the tool connection portion 48 is illustrated to only include the exterior housing for clarity of the current discussion. As illustrated in FIG. 4 and FIG. 5, however, the tool assembly or portion may include the collet or engagement portion 48 and the working or operating portion 50.

Figure 4:
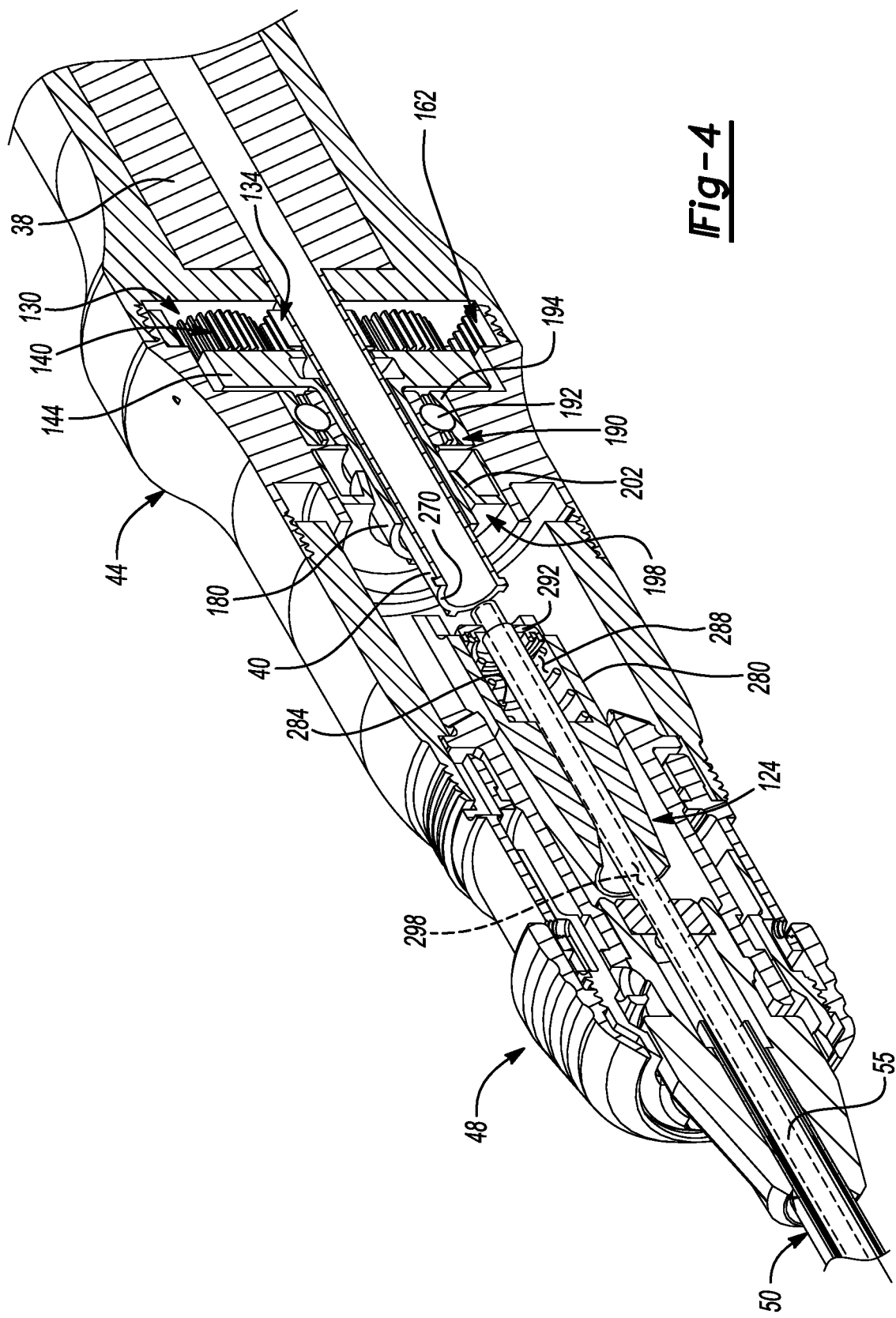
FIG. 4 is a perspective cross-sectional view of FIG. 3.
Figure 5:
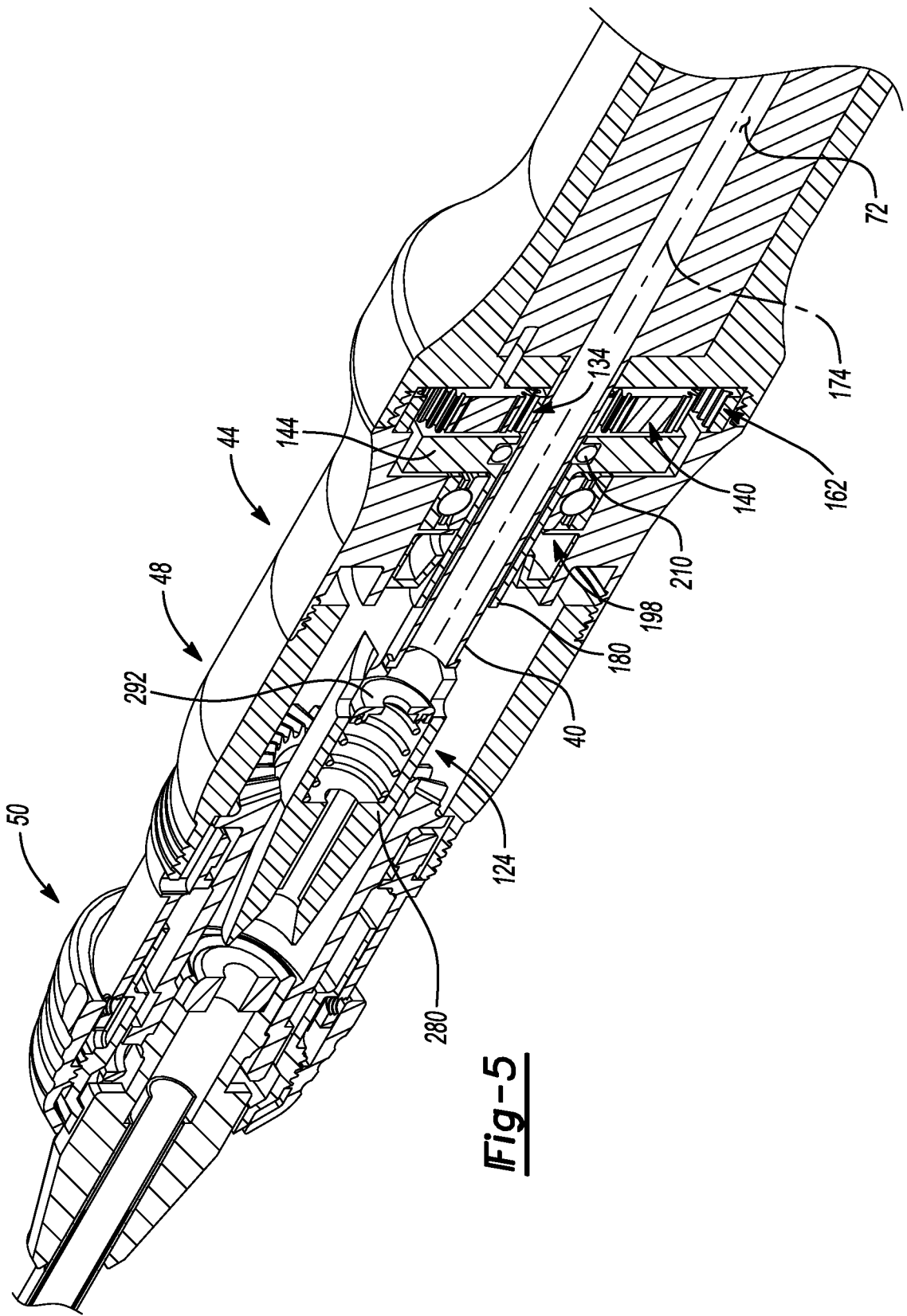
FIG. 5 is a distal end perspective view of the cross-sectional view of FIG. 3.

With continuing reference to FIGS. 4 and 5, the tool portion 50 may, therefore, include the shaft or elongated portion 55 that extends from the distal or working end tip 54 to a drive shaft engaging portion or assembly 124. In various embodiments, for example, the drive shaft engaging portion 124 may engage the drive shaft 40 to be driven by the motor 38. The drive shaft 40 may extend through the gearing assembly 44 and directly engage the tool portion 50 at the drive shaft engaging portion 124. In various embodiments for example, a direct connection of the drive shaft 40 with the drive shaft connection assembly 124 may provide for a high speed operation of the tool tip 54. A high speed operation of the tool tip 54, however, may provide a low torque at the tool tip 54. Therefore, in various embodiments, the tip 54 may be operated in a high speed and low torque configuration.

As illustrated in FIG. 4 and FIG. 5, the drive shaft engaging assembly 124 may directly engage the drive shaft 40. The drive shaft 40, however, may include assemblies or portion to engage a gearing assembly 130 within the gear housing 44. The gear assembly 130 may include a planetary gear assembly and the gearing assembly may be referred to as a planetary gearing assembly 130 herein. With continuing reference to FIGS. 2-5, and additional reference to FIG. 6, the gear assembly 130 may include various gear portions. For example, the gear assembly 130 may include a sun gear 134 that includes an external tooth or engagement 136. The sun gear 134 may be formed separately from the drive shaft 40 and/or formed as a single portion therewith (e.g. machine on the drive shaft 40). In various embodiments, however, the sun gear 134 may be formed separately and fixed to the drive shaft 40, such as with welding, adhesives, or the like. If the sun gear 134 is formed directly onto or as a single machined portion of the drive shaft 40, the teeth or gears 136 may be formed onto the drive shaft 40 as the sun gear. The sun gear may engage with one or more planetary gears, including planetary gears 140 (wherein individual gears are augmented by a lowercase letter). The planetary gears 140 may include three planetary gears 140a, 140b, and 140c. It is understood, however, that any appropriate number of planetary gears 140 may be provided, and three is merely exemplary. Each of the planetary gears are held on a carrier 144. The carrier 144 may include a plurality of axels or spindles 148 (wherein individual axle are augmented by a lowercase letter) for each of the planetary gears 140, respectively. Accordingly, each of the planetary gears 140 may include an internal bore 152 to be placed on the respective axle 148.

Each of the planetary gears 140 include external teeth 154. The external teeth 154 may engage the external teeth 136 of the sun gear. Further, the external teeth 154 engage internal teeth 158 of a ring gear 162. The planetary gears 154, therefore, engage the teeth 158 of the ring gear 162 and the external teeth 136 of the sun gear 134. As discussed above, the sun gear 134 may be formed on the shaft 40.

The ring gear 62 may also be fixed within the gear housing 44, in any appropriate manner. For example, the ring gear 162 may be machined as a single piece with the housing 44. In various and/or alternative embodiments, however, the ring gear 162 may be formed separately from the housing 44 and fixed thereto. For example, the ring gear 162 may be welded, adhered, or the like to the housing 44. The ring gear 162 may be mechanically and/or chemically fixed to the housing 44.

Figure 6:
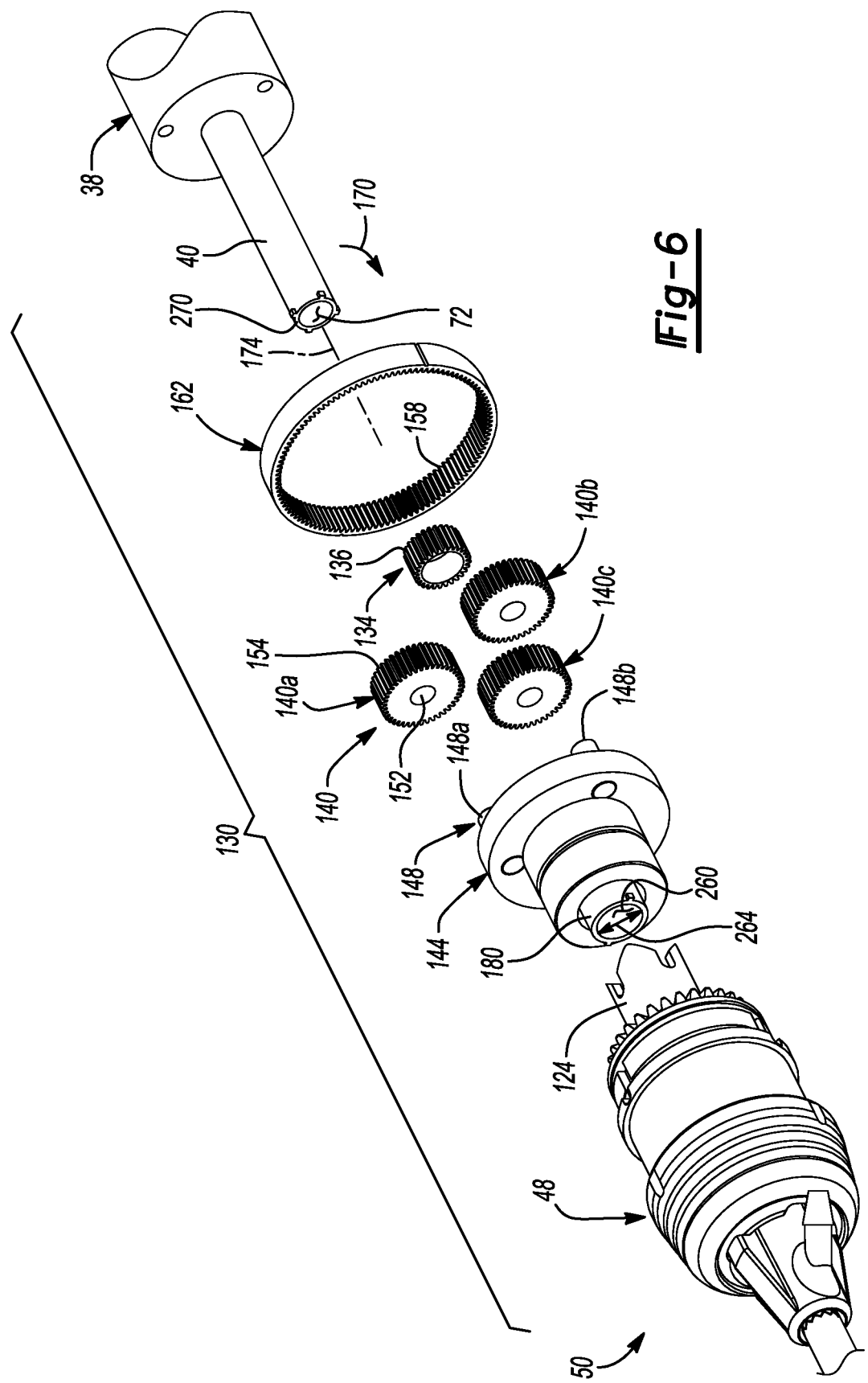
FIG. 6 is an exploded view of a gearing assembly of the instrument.
Figure 7:
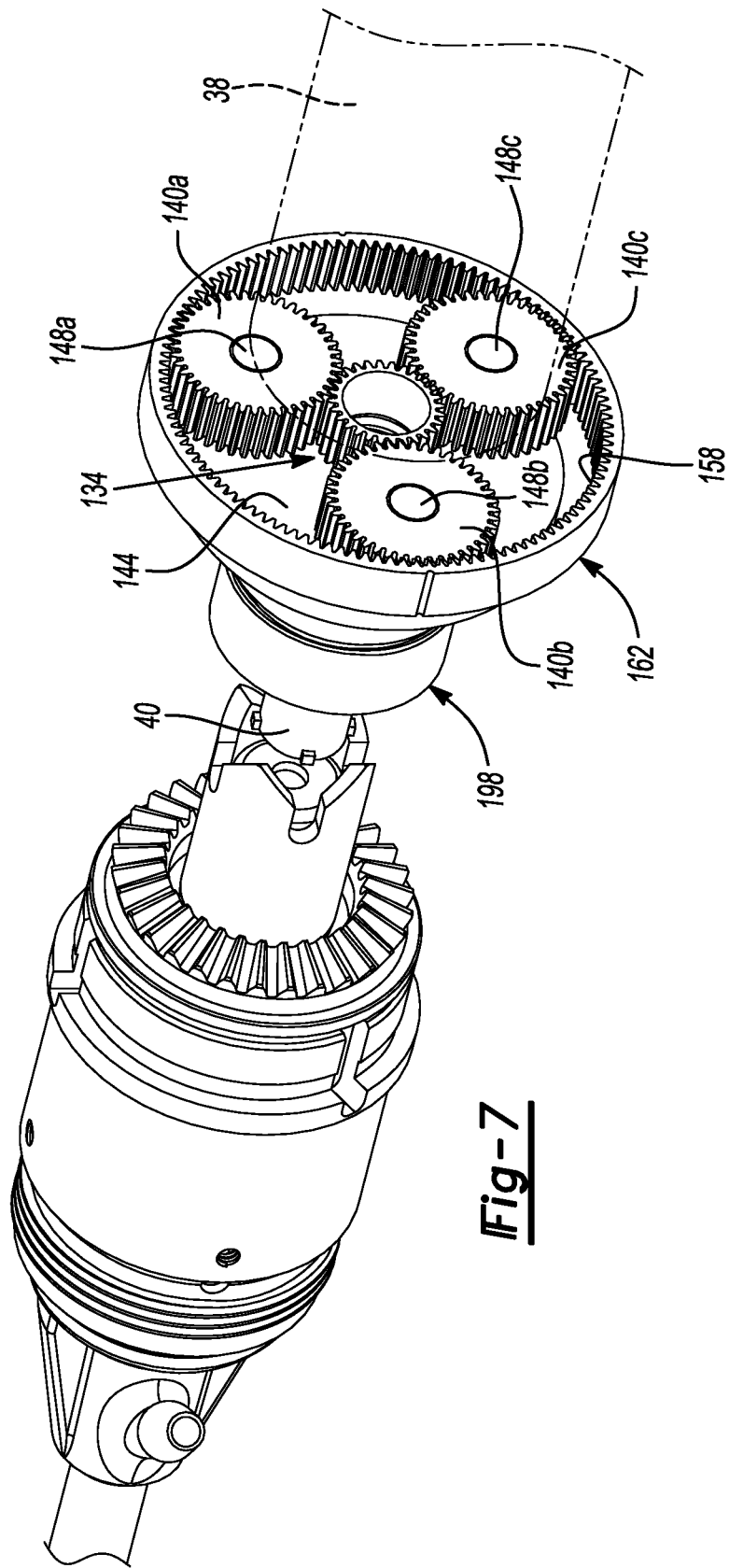
FIG. 7 is a partial exploded view from a proximal end of the gearing assembly.

With continuing reference to FIG. 6, and additional reference to FIG. 7, the carrier 144 may rotate within the housing 44. As the ring gear 162 is fixed to the gear housing 44, rotation of the shaft 40, such as in the direction of arrow 170 around an axis 174 of the shaft 40, causes the sun gear 134 to rotate and the external teeth 136 to engage the external teeth 154 of each of the respective planetary gears. Again, as the ring gear 162 is fixed, the internal teeth 158 engage the external teeth 154 of the planetary gears as the shaft 40 rotates the sun gear 134. Fixed to the carrier 144 is the secondary or external drive shaft 180. The external drive shaft 180 may also be referred to as a carrier drive shaft 180. The carrier drive shaft 180 rotates when the carrier 144 rotates due to the engagement of the planetary gears 140, the sun gear 134. Thus, rotation of the drive shaft 40 rotates the sun gear 134, which in turn rotates the planetary gears 140 within the rain gear 162 causing the carrier 144 to rotate, also generally in the same direction as the drive shaft 40. This causes the secondary drive shaft 180 to also rotate, generally in the same direction as the drive shaft 40.

Figure 8:
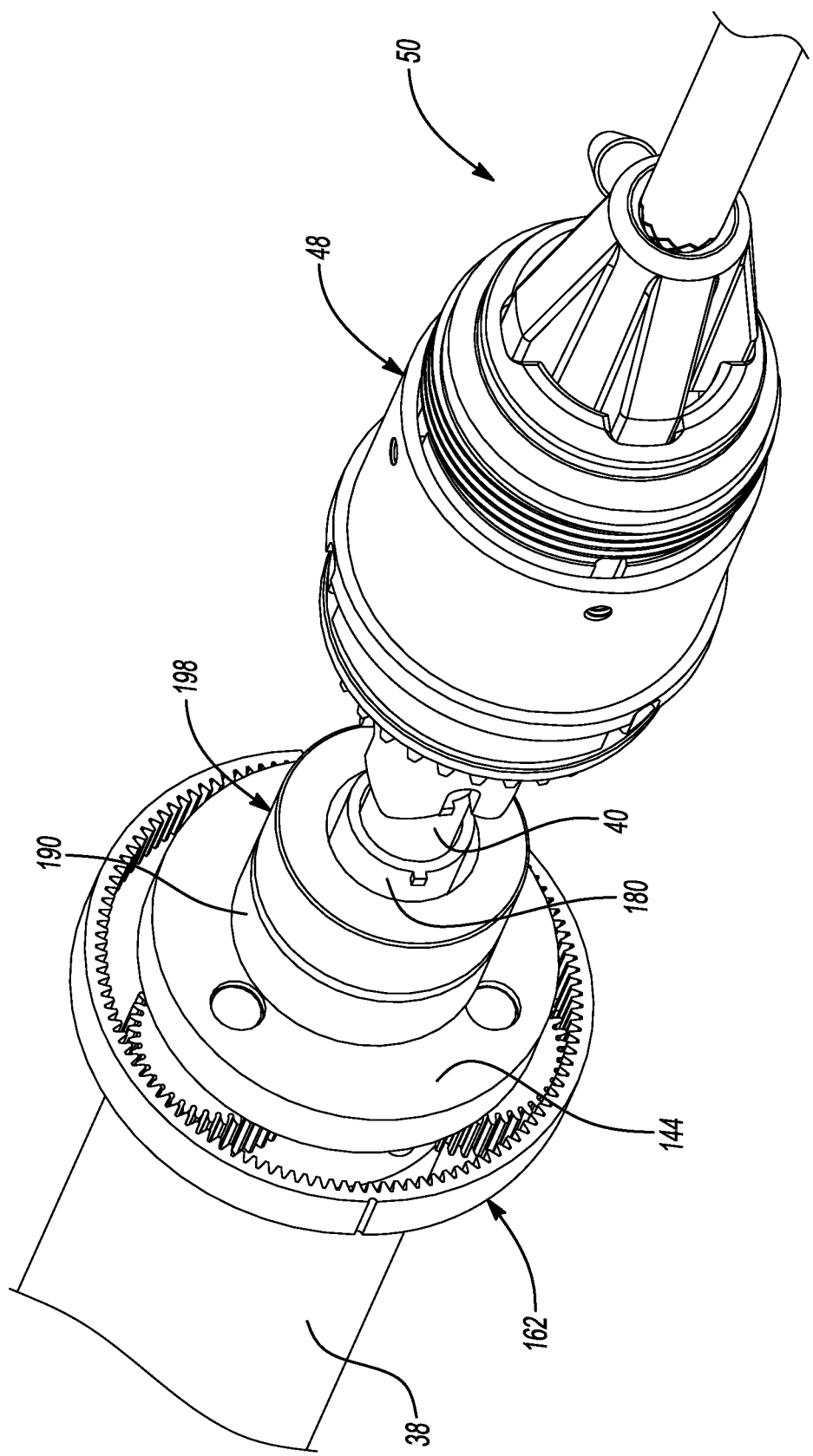
FIG. 8 is a partial exploded view from a distal end of the gearing assembly.

With continuing reference to FIGS. 3-7, and additional reference to FIG. 8, the gear assembly 44 may further include various seals, bearings, and the like. For example, a bearing assembly 190 may include a sealed wall bearing assembly including one or more bearing balls 192 sealed within a sealed race assembly or track 194. In addition, one or more sealing members, such as a lip seal 198 may be provided to surround the second drive shaft 180 to assist in sealing the gearing assembly 44 and the motor 38. The seal 198 may be referred to as a lip seal having a sealing surface or section 202 that engages an exterior portion of the drive shaft 180. The gearing assembly 44 may further include a further bearing/seal assembly 210 that may be positioned within the carrier 144. The second bearing assembly 210, may not be necessary, but may be provided to assist in providing additional stability, such as radial stability relative to the axis 174.

As discussed above, and illustrated in the various drawings, the tool assembly portion 50 includes the drive shaft engaging section or portion 124 that may selectively engage at least one of the two drive shafts 140, 180. Both of the drive shafts may rotate during operation of the motor 38 due to the spinning of the main or direct drive shaft 40 extending from the motor 38 and including the sun gear connected with the drive shaft 40. As discussed above the sun gear 134 may be fixed to the drive shaft 40 in any appropriate manner, such as being machined or formed as a single piece with the drive shaft 40, fixed to the drive shaft after formation of the sun gear 134, or any other appropriate mechanism. Nevertheless, rotation of the sun gear 134 (i.e. due to rotation of the drive shaft 40) causes rotation of the planetary gear system 130 including the planetary gears 140, and the carrier 144. Rotation of the carrier 144 causes rotation of the second drive shaft 180 as the second drive shaft 180 extends from the carrier 144. In various embodiments, the second drive shaft 180 may be formed as a single piece with the carrier 144. In various embodiments, however, the second drive shaft 180 may be formed as a second portion that is mounted or fixed to the carrier 144. Nevertheless, the second drive shaft 180 generally rotates with the carrier 144 due to rotation of the main or first drive shaft 40.

Figure 9:
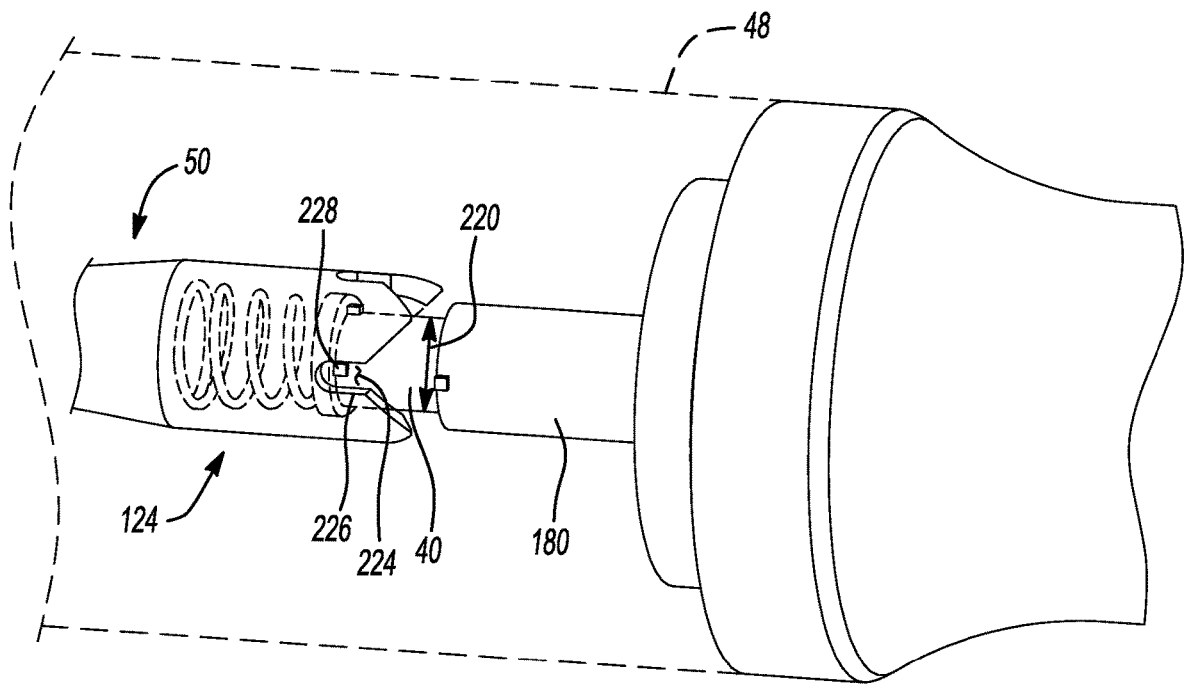
FIG. 9 is a detail view of a first drive shaft engaging a first tool.
Figure 10:
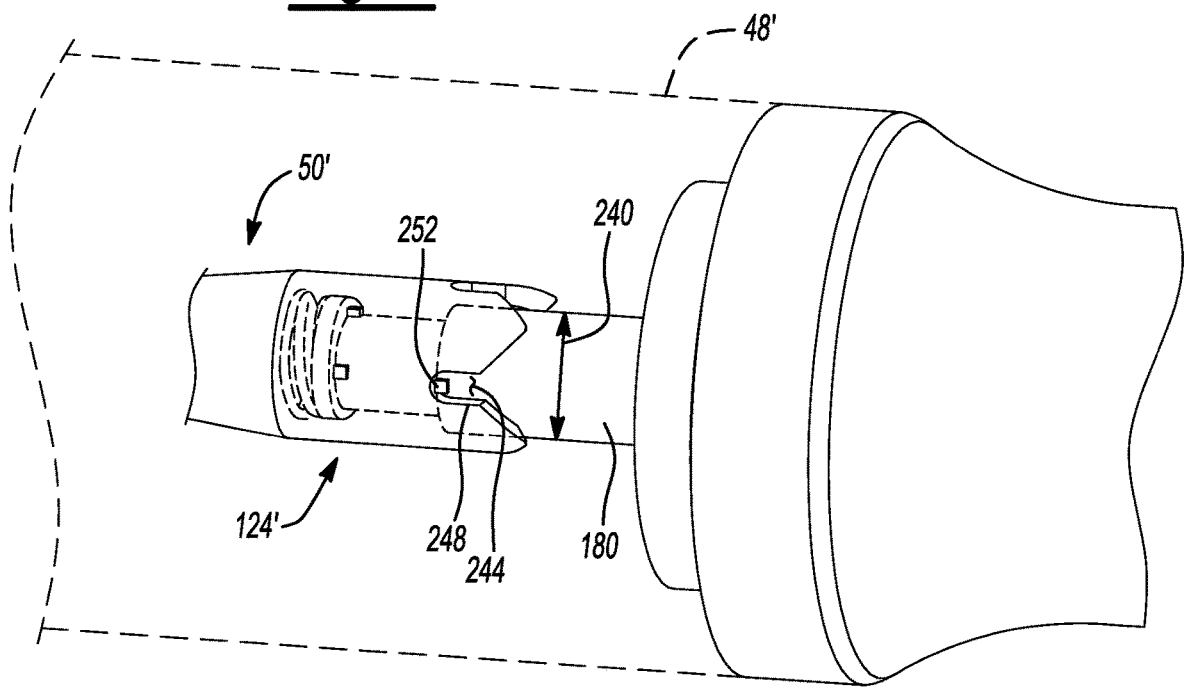
FIG. 10 is a detail view of a second drive shaft engaging a second tool.

With reference to FIGS. 6-8 and additional reference to FIGS. 9 and 10, the drive shafts 40, 180 may selectively be engaged by drive shaft connection portions including the drive shaft connection portion 124 that may engage the drive shaft 40 (FIG. 9) or a drive shaft engagement portion 124' that may engage the drive shaft 180 (FIG. 10). The drive shaft connection portions 124, 124' may be substantially identical save for a selected internal diameter to engage the shaft 40 by the drive shaft engagement portion 124 or to engage the drive shaft 180 by the drive shaft engagement portion 124'. Specifically, the drive shaft engagement portion 124 may include an internal diameter that is configured to engage an external diameter 220 of the drive shaft 40. The drive shaft engagement portion may include one or more indents or troughs 224 that may be defined by walls or fingers 226 to engage one or more protrusions 228 that extend from an exterior wall of the drive shaft 40. The protrusion 228 may engage the side wall 226 and transmit a force or rotation thereto to rotate selected portions of the tool assembly 50, including the distal tip 54, as discussed above.

Similarly, the second or larger drive shaft engagement section 124' may include an internal diameter configured to engage an external diameter 240 of the drive shaft 180 which may be greater than the diameter 220 of the drive shaft 40. The drive shaft engagement portion 124' may further include troughs 244 that are defined by the side walls 248. Again, the drive shaft 180 may include one or more protrusions 252 to be received and/or engage the side walls 248 so that rotation may be imparted to the tool assembly 50.

The drive shaft engagement portion 124' may be part of a different or alternative tool portion which may be referred to as a second or alternative tool portion 50'. In various embodiments the tool portion 50 that engages the drive shaft 40 may be a high speed tool or high speed and a lower torque may be transmitted to the tool tip 52. The second tool 50' that includes the drive shaft engaging portion 124' to engage the drive shaft 180 may be a low speed high torque tool so that a lower speed and a higher torque transmitted to the tool tip 52.

Accordingly, multiple tool assemblies 50, 50' may be used to engage or disengage selected tools to the separate drive shafts 40, 180, respectively or selectively. In other words, more than one told assembly 50 may engage separate drive shafts within the instrument assembly 30 for operation of the tool tip 54. Thus, the single handle assembly including the motor 38 may be used to power at least two different tool portions 50, 50' in a selected manner by engagement of a selected one of the drive shafts 40, 180. This allows the single instrument assembly 30 to operate more than one tool tip in more than one manner.

With continuing reference to FIGS. 6-10, each of the drive shaft engagement sections 124 may include selected features and portions. As discussed above, the drive shaft 40 may include the external diameter 220 that may be allowed to pass through an internal bore or cannula 260 of the second drive shaft 180 that includes a diameter or internal diameter 264. The first drive shaft 40 includes the bore or cannula 72 that may allow for suction through the instrument assembly 30. To allow or ensure efficient suction a seal may be made to a distal end 270 of the drive shaft 40 with both of the drive shaft engagement sections 124, 124'. Accordingly, discussion of the drive shaft connection portion 124 further herein is intended to refer to both of the drive shaft engagement portions 124, 124' as it will substantially differ only in internal diameters to engage respective external diameters 220, 240.

With reference to FIGS. 4 and 5, the drive shaft engagement section may include the external engagement feature or body 280 that defines the respective troughs and edge walls to engage the respective projections 228, 252 of the respective drive shafts 40, 180. Within the body 280 may be a biasing member 284. The biasing member may be any appropriate biasing member such as a coil spring. The coil spring 284 may be held within a cavity 288 of the body 280. A seal member 292 may be positioned proximally in the body 280 to engage the distal end 270 of the drive shaft 40. Thus, a seal may be formed around the drive shaft 40 relative to the body 280. As further illustrated in FIG. 4, the tool shaft 55 may extend through the body 280. In various embodiments, the tool shaft 55 may further include a bore or cannula 298 thus due to the seal 292 a suction may be drawn through the cannula 72 and further through the cannula 298 in the tool shaft 55.

The drive shaft engagement bodies 124, 124' may include similar portions that may be sized to fit the respective tool bodies 280 of the respective drive shaft engagement portions 124, 124'. Nevertheless, each may include a seal that is configured to seal to the drive shaft 40 whether rotation is provided directly by the drive shaft 40 or by the second drive shaft 180. The drive shaft 40 may rotate relative to the sealing member 292 at a speed different than the secondary shaft 180 due to the formation and/or configuration of the sealing member 292. The sealing portion may be formed of an appropriate material such as nitrile, hydrogenated nitrile, fluoroelastomer, polyacrylate, silicone, Polytetrafluoroethylene (PTFE), ethylene propylene diene monomer, chloroprene, polyurethane. It is further understood that the sealing portion 292 may be formed similar to the seal 198. The seal 198 may be referred to as a lip seal and a lip seal may also be provided as the sealing member 292 in the drive shaft engagement body 280 of the respective drive shaft engagement portions 124, 124'.

The instrument assembly 30, therefore, as discussed above, may provide an instrument to power more than one tool or portion at more than one speed and/or torque. The instrument assembly 30, therefore, may be used to power a plurality of tool portions at different speeds and/or torques without requiring varying speed of the motor 38 or other inputs from the user 24. In various embodiments, a kit may include at least two tool portions. In the kit, a first tool portion is configured to be operated at a high torque and low speed and the second tool at a high speed and low torque. It is understood, however, that a kit may include any appropriate number of tools. Further, a high torque may be provided without requiring a selected or different motor 38 in the instrument assembly 30. Thus the instrument assembly 30 may be used to perform a procedure on the subject 60 without requiring multiple motor handles or housings 34 to be used with different tool assemblies 50 for various portions of the procedure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An instrument assembly for performing a procedure, comprising:
    a first drive shaft extending distally from a motor and connected directly to and powered by the motor;
    a gear assembly configured to be moved by rotation of the first drive shaft; and
    a second drive shaft operably connected to the gear assembly;
    wherein a first output of the first drive shaft is different than a second output of the second drive shaft when driven by the motor;
    wherein the first drive shaft is configured to directly engage a first tool assembly having a first working end configured to perform the procedure on a subject;
    wherein the second drive shaft is configured to directly engage a second tool assembly having a second working end configured to perform the procedure on the subject;
    wherein at least one of:
    the first tool assembly having a first drive shaft engaging portion configured to directly engage the first drive shaft; or
    the second tool assembly having a second drive shaft engaging portion configured to directly engage and rotationally drive the second drive shaft, the second drive shaft engaging portion including a seal that is configured to engage the first drive shaft; and
    wherein
        the first output includes a first speed and a first torque;
        the second output includes a second speed and a second torque;
        the first speed is greater than the second speed; and
        the first torque is less than the second torque.

2. The instrument assembly of claim 1, wherein the gear assembly comprises:
    a sun gear;
    a planetary gear;
    a ring gear; and
    a carrier carrying at least the planetary gear;
    wherein the first drive shaft drives the sun gear;
    wherein the second drive shaft is connected to the carrier.

3. The instrument assembly of claim 2, wherein the sun gear is formed with the first drive shaft.

4. The instrument assembly of claim 2, wherein the first drive shaft and the second drive shaft are concentric.

5. The instrument assembly of claim 1, wherein the motor powers both the first drive shaft and the second drive shaft simultaneously.

6. An instrument assembly for performing a procedure, comprising:
    a first tool assembly having a first drive shaft engaging portion and a first working end, the first drive shaft engaging portion configured to directly engage a first drive shaft and the first working end configured to perform the procedure on a subject; and
    a second tool assembly having a second drive shaft engaging portion and a second working end, the second drive shaft engaging portion configured to directly engage a second drive shaft and the second working end configured to perform the procedure on the subject;
    wherein both the first drive shaft and the second drive shaft extend distally from and are driven by a single motor in an instrument handle assembly;
    wherein the second drive shaft engaging portion is rotationally driven by the second drive shaft;
    wherein the second drive shaft engaging portion includes a seal that is configured to engage the first drive shaft.

7. The instrument assembly of claim 6, wherein the instrument handle assembly comprises:
    the first drive shaft extending from the single motor and connected directly to and powered by the motor;
    a gear assembly configured to be moved by rotation of the first drive shaft; and
    the second drive shaft operably connected to the gear assembly;
    wherein a first output of the first drive shaft is different than a second output of the second drive shaft when driven by the motor.

8. The instrument assembly of claim 7, wherein the gear assembly comprises:
    a sun gear;
    a planetary gear;
    a ring gear; and
    a carrier carrying at least the planetary gear;
    wherein the first drive shaft drives the sun gear;
    wherein the second drive shaft is connected to the carrier.

* * * * *